United States Patent [19]

Johnson et al.

[11] Patent Number: 5,677,495

[45] Date of Patent: Oct. 14, 1997

[54] COMPRESSIVE STRENGTH TESTING OF HPC CYLINDERS UTILIZING CONFINED CAPS

[76] Inventors: Claude Derrell Johnson, Box 401, South Gillies, Ontario, Canada, P0T 2V0; S. Ali Mirza, 1508-590 Beverly Street, Thunder Bay, Ontario, Canada, P7B 6H1; Eric Powell, R.R. #13, Site 14-Box 12, Thunder Bay, Ontario, Canada, P7B 534; Edith Ramanathan, 2537 Cypress Drive, Thunder Bay, Ontario, Canada, P7J 1A2

[21] Appl. No.: 458,897

[22] Filed: Jun. 2, 1995

[51] Int. Cl.$^6$ ........................................ G01N 3/02
[52] U.S. Cl. ........................................ 73/856; 73/818
[58] Field of Search ................... 73/818, 825, 849, 73/846, 853, 855, 856, 857

[56] References Cited

U.S. PATENT DOCUMENTS

| | | | |
|---|---|---|---|
| 2,864,253 | 12/1958 | Lenton | 73/825 |
| 3,545,263 | 12/1970 | Hadley et al. | 73/825 |
| 3,593,573 | 7/1971 | Ely et al. | 73/825 |
| 3,757,568 | 9/1973 | Fletcher et al. | 73/94 |
| 3,975,950 | 8/1976 | Erdei | 73/94 |
| 4,044,091 | 8/1977 | Hurst | 264/251 |
| 4,071,996 | 2/1978 | Muto et al. | 52/741 |
| 4,534,225 | 8/1985 | Peacock et al. | 73/860 |
| 4,752,431 | 6/1988 | Knowles | 264/512 |
| 4,981,626 | 1/1991 | Uchizaki | 264/23 |
| 5,043,033 | 8/1991 | Fyfe | 156/71 |
| 5,327,694 | 7/1994 | Gamel et al. | 52/727 |
| 5,435,187 | 7/1995 | Ewy et al. | 73/856 |

FOREIGN PATENT DOCUMENTS

| | | |
|---|---|---|
| 2398297 | 7/1977 | France. |
| 905708 | 2/1982 | U.S.S.R. . |

OTHER PUBLICATIONS

U.S. Army Engineer Waterways Experiment Station Miscellaneous Paper C–72–12 *Effect of Method of Preparation of Ends Concrete Cylinders for Testing–* K.L. Saucier.

*Primary Examiner*—Hezron E. Williams
*Assistant Examiner*—Max H. Noori
*Attorney, Agent, or Firm*—Murray E. Thrift; Adriian D. Battison

[57] ABSTRACT

A confined capping system provides a simple approach for compressive strength testing of high performance concrete specimens. The test specimen ends are capped with a conventional capping compound confined in steel rings larger in diameter than the specimen. The capped rings are compression tested in a conventional way. This method thus employs standard concrete laboratory testing equipment. An inexpensive customized capping apparatus may be used for preparing the specimen ends. The method ensures that confinement is provided to the cap without having to place tight controls on specimen end roughness prior to capping and on the cap thickness itself.

15 Claims, 6 Drawing Sheets

FIG. 2

FIG.4 AVERAGE COMPRESSIVE STRENGTH OF CYLINDERS WITH CONFINED CAPS TESTED AT VARIOUS AGES FOR CONCRETE MIX DM9-1

FIG.5 AVERAGE COMPRESSIVE STRENGTH OF CYLINDERS WITH CONFINED CAPS TESTED AT VARIOUS AGES FOR CONCRETE MIX DM19-1

FIG. 6 AVERAGE COMPRESSIVE STRENGTH OF CYLINDERS RELATIVE TO STRENGTH OF STANDARD 150 X 300 MM CYLINDERS WITH GROUND ENDS

FIG. 7 AVERAGE COMPRESSIVE STRENGTH OF CYLINDERS RELATIVE TO STRENGTH OF CYLINDERS OF SAME SIZE WITH GROUND ENDS

COMPRESSIVE STRENGTH TESTING OF HPC CYLINDERS UTILIZING CONFINED CAPS

FIELD OF THE INVENTION

The present invention relates to concrete testing and more particularly to the testing of compressive strength in high performance concrete.

BACKGROUND

The high performance concretes to which the present invention relates are those with compressive strengths in the order of 100 MPa and greater. For such concretes, a standard procedure for compressive strength testing has yet to be developed. At present, specimens of different sizes and shapes are being used and a number of different procedures are being followed to prepare the end conditions of specimens for compressive strength testing. These factors can have a significant effect on the measured compressive strength of high performance concrete. To obtain consistent test results and an accurate measure of the compressive strength rather than just a measure of the shortcomings of the testing equipment and procedure, these factors need to be carefully controlled.

For normal strength concrete testing, capped end conditions are a standard and sulfur capping compounds with compressive strengths on the order of 50 MPa are readily available for this use. If standard capping procedures are employed, these capping compounds are not of sufficient strength for use in the testing of high performance concretes which have compressive strengths on the order of 100 MPa or higher.

The testing of concretes using capping compounds with and without confining rings was reported in Saucier, K. L., 1972; Effect of Method of Preparation of Ends of Concrete Cylinders for Testing; U.S. Army Engineer Waterways Experiment Station, Vicksburg, Miss.; Miscellaneous Paper C-72-12. While that paper refers to the testing of "high-strength" concrete, the compressive strength of the concrete used was about 69 MPa, near the upper limit of normal strength concrete. The paper concludes that the confining of end caps in rings is of little use. It is concluded that: "It is not practical to confine a weak capping material sufficiently to produce a state of high stress resistance in the material and allow high-strength concrete cylinders to attain maximum strength." It is also concluded that: "Confinement in rings does not improve the performance of high-strength caps on high-strength concrete, but may enhance cap performance under other conditions, i.e. weak capping material on high strength concrete, although not necessarily to a degree adequate to mobilize the full strength of the specimen."

A test method which uses a neoprene pad in a steel restraining pot at each end of a cylindrical specimen, reported in Carrasquillo, P. M., and Carrasquillo, R. L., 1988; Effect of Using Unbonded Capping Systems On the Compressive Strength of Concrete Cylinders, ACI Materials Journal, 85(3): 141–147 seems to have provided satisfactory results for concrete strengths up to 76 MPa. However, for higher strengths, the neoprene pads must be changed for each cylinder tested, making the method uneconomical for high performance concretes (Boulay and deLarrard 1993, infra).

Another method of end capping which uses the so-called "sand box" has been recently reported in Boulay, Claude, and deLarrard, Francois, 1993; A New Capping System for Testing HPC Cylinders: The Sand-Box; Concrete International, 15(4): 63–66. This method requires an elaborate preparation of the cylinder ends, making it cumbersome for laboratory use and impractical for field testing.

Because of this, the ends of high performance concrete specimens are usually prepared by grinding the ends to form two relatively smooth plane, parallel surfaces. A specially designed grinding machine is usually employed to accomplish this objective. Some laboratories have adapted a large metal lathe for this purpose. The purchase of either of these pieces of equipment can amount to a sizable capital outlay.

SUMMARY

It has now been discovered that, contrary to what might be expected from Saucier (supra) it is possible to test high performance concretes using conventional capping compounds if the caps are confined.

The present invention provides a simple test method for the compressive strength testing of high performance concretes that may employ standard concrete laboratory testing equipment and an inexpensive capping apparatus for preparing specimen end conditions.

According to one aspect of the present invention there is provided a method of compressive strength testing of high performance concrete having an anticipated minimum compressive strength, the method comprising:

providing a test specimen of the concrete;

capping opposite ends of the test specimen with a capping compound having a compressive strength substantially less than said anticipated minimum compressive strength;

confining the capping compound at each end of the test specimen with a ring surrounding the capping compound and the end of the test specimen, the ring having a tensile strength greater than that of the capping compound; and testing the specimen for compressive strength.

According to another aspect of the present invention there is provided a test specimen of high performance concrete comprising:

a specimen of the concrete;

two caps covering respective ends of the specimen, each cap comprising a disk of capping material covering the end of the specimen and a ring surrounding the disk, the ring having a tensile strength greater than that of the capping material.

The role of the ring at each end of the specimen is to provide lateral confinement for the specimen caps. This confinement restricts the lateral deformation of the cap, thus increasing its vertical compressive strength.

According to a further aspect of the present invention there is provided apparatus for preparing a test specimen of high performance concrete, said apparatus comprising:

a base plate having a smooth upper surface;

ring confining means for holding a confining ring at a predetermined position on the upper surface of the base plate; and specimen centering means for engaging a specimen of the concrete and centering the specimen on the ring.

In use of the capping guide, the ring is held in place and filled with liquid capping compound. The test specimen is then placed in the apparatus, with one end in the capping compound. Once the capping compound has set, the other end of the specimen may be capped in the same way.

Specimens commonly used for compressive strength testing are cylindrical in shape. Consequently, in the following there are several references to cylindrical specimens or cylinders. It is to be understood however, that the invention is also applicable to specimens of other shapes, for example prisms.

Another problem that may arise is the ability of the testing machine to handle high performance concrete specimens. With compressive strengths of high performance concretes now on the order of 100 MPa being fairly common, a testing machine with a capacity of 2500 kN is required to test a 150×300 mm cylinder. A testing machine of this capacity may not even be adequate if the actual design overcapacity of the machine does not make the testing machine stiff enough. Testing machines used in the compressive strength testing of high performance concretes must be relatively stiff so that the elasticity of the machine itself does not produce a sudden release of energy at the time of the specimen failure that will seriously affect the measured test result. In Lessard, Michel; Chaalial, Omar; and Aitcin, Pierre-Claude, 1993; Testing High-Strength Concrete Compressive Strength; ACI Materials Journal, 90(4): 303-308, it is recommended that the testing machine capacity should be approximately 1.5 times the average expected cylinder strength, primarily for the testing machine characteristics to be stiff enough but also because a sudden release in energy can affect the calibration of the testing machine. Although this does seem like a reasonable guideline to follow, the actual design and overcapacity of the testing machine should be considered in making this judgment. It is noted that by the criterion recommended by Lessard et al., testing machine capacities of 2650 kN and 4000 kN would be required for the testing of 150×300 mm cylinders at compressive strengths of 100 MPa and 150 MPa, respectively. Many concrete testing laboratories that are set up for testing normal strength concrete do not have testing machines with these capacities.

As a consequence, 100×200 mm cylinders are gaining more acceptance in the literature. This, or some other specimen size, may emerge as a standard specimen size used in the compressive testing of high performance concretes. Using the previously stated criterion, 100 MPa and 150 MPa concrete cylinders of 100×200 mm size could be tested with 1200 kN and 1800 kN capacity testing machines, respectively. Machines with load capacities of these orders of magnitude are commonly available in most concrete testing laboratories. Of course, the maximum aggregate size used in the specimen must be taken into consideration when selecting the appropriate cylinder size. It is to be understood that the use of rings for confining the end caps is independent of specimen dimensions.

BRIEF DESCRIPTION OF THE DRAWINGS

In the accompanying drawings, which illustrate exemplary embodiments of the invention in its various aspects, and graphical test results.

DETAILED DESCRIPTION

Figure 1:
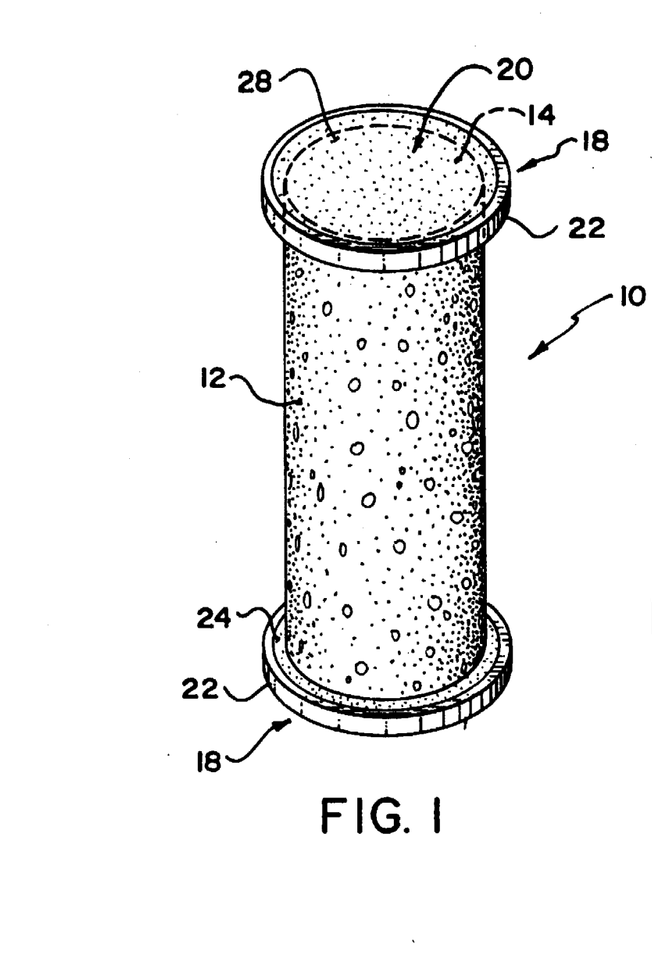
FIG. 1 is an isometric view of a test cylinder prepared according to the present invention.
Figure 2:
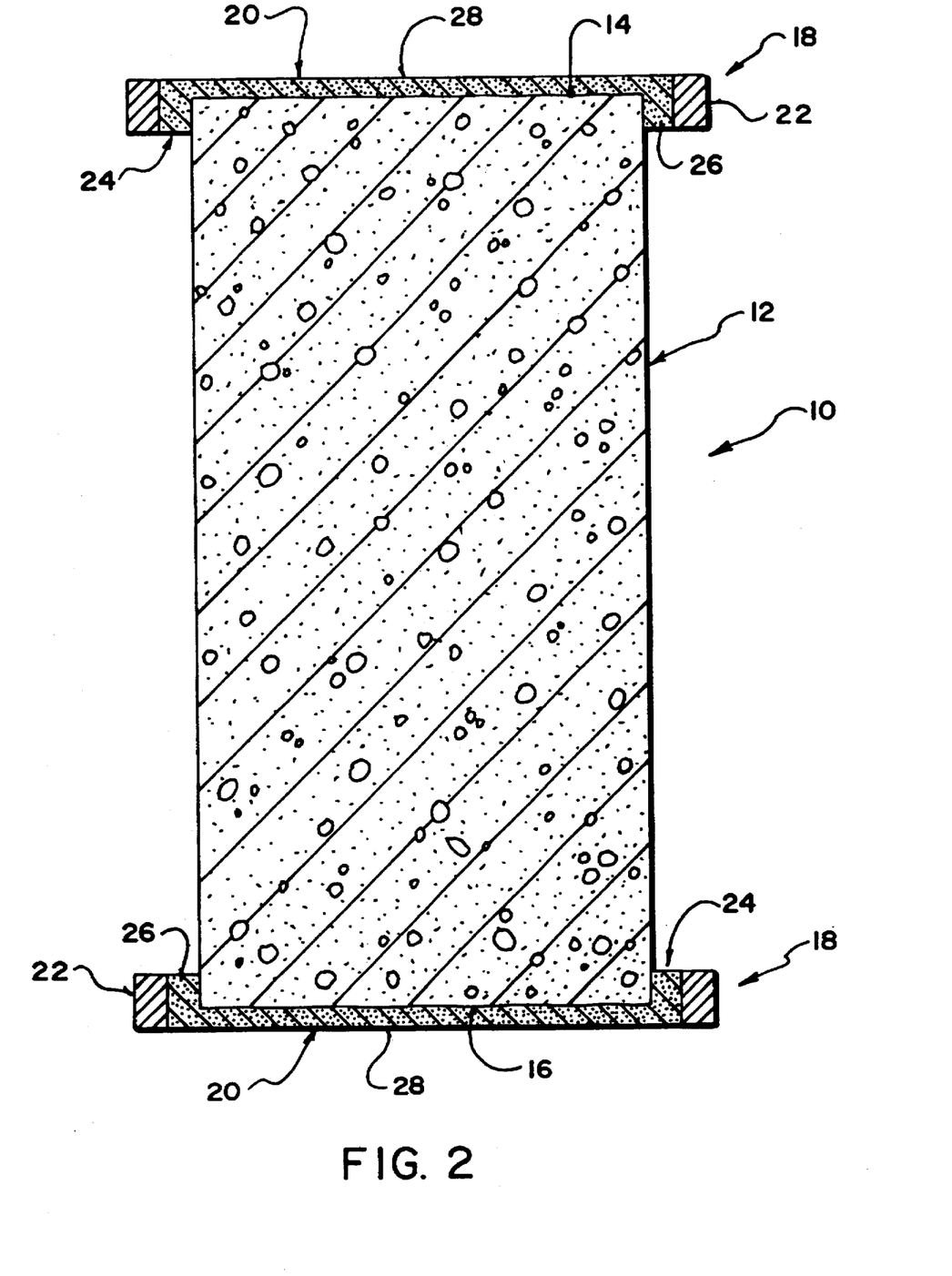
FIG. 2 is a side view, partly in section of the cylinder of FIG. 1.

Referring to the accompanying drawings, and especially FIGS. 1 and 2, there is illustrated a concrete test cylinder 10 having a cylindrical side wall 12 and two ends 14 and 16. On each of the ends is a cap 18. The cap is a disk 20 of conventional capping material surrounded by a steel ring 22. The ring has a resistance to deformation greater than that of the disk so as to confine the disk against spreading laterally when it is compressed vertically. The ring has an inner diameter greater than the outer diameter of the cylinder to provide an annular space 24 between the two. An annulus 26 of the capping material extends along the side wall of the cylinder to fill the space 26. Each of the end caps has a smooth end surface 28 for substantially uniform engagement with the testing machine.

Figure 3:
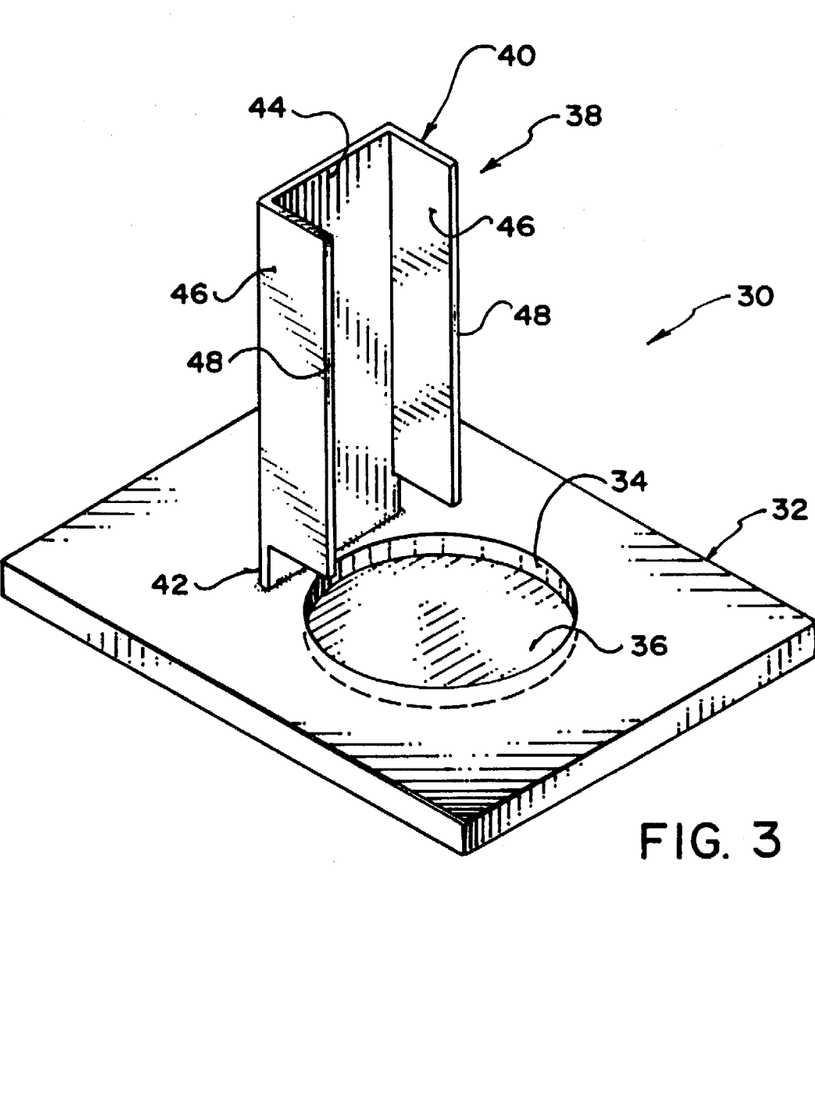
FIG. 3 is an isometric view of a capping guide according to the present invention.

The end capping is performed using a capping guide 30 illustrated in FIG. 3. This guide includes a base plate 32 with a circular recess 34 in its upper surface. The base of the recess is a smooth surface 36. The inside diameter of the recess is slightly greater than the outside diameter of the ring 22 so that the ring can be centered and confined in the recess. Beside the recess is a cylinder centering guide 38. This includes a channel 40 supported in an upright position on the base plate 32 by a short plate 42 that is an integral extension of the channel web 44. The two flanges 46 of the channel project from the web over the edge of the recess 34 so that the parallel free edges 48 of the flanges are perpendicular to the recess surface 36 and will engage the side of a concrete test cylinder to support it in alignment with the recess 34.

Examples of the preparation and testing of concrete specimens according to the present invention will be described in the following by way of example to illustrate the efficacy of the present invention.

CONCRETE MIXES AND SPECIMEN PREPARATION

Fifty-five test cylinders 100×200 mm and 150×300 mm in size were cast from three different high performance concrete mixes and tested to establish the suitability of the testing method. Mix proportions including cement, silica fume, water, aggregates, and naphthalene-based superplasticizer are given in Table 1.

Two mixes, DM9-1 and DM19-1, had the same water-to-cementitious material ratio of 0.23 but different maximum aggregate sizes of 9 mm and 19 mm, respectively, as well as different aggregate blends. Mix DM9-2 was similar to mix DM9-1 except that the water-to-cementitious material ratio was held to 0.20. The coarse aggregate used in all mixes was crushed Manitoulin Island dolomite and the fine aggregate had a fineness modulus of 2.6.

TABLE 1

| Material (per m | Concrete mix proportions | | |
|---|---|---|---|
| | Mix DM9-1 | Mix DM9-2 | Mix DM19-1 |
| Cement (kg) | 495 | 495 | 495 |
| Silica fume (kg) | 55 | 55 | 55 |
| Water (L) | 126.5 | 110.0 | 126.5 |
| | (120.5)* | (104.0)* | (118.5)* |
| Superplasticizer (L) | 19 | 20 | 20 |
| Coarse aggregate (kg) | 1169 | 1169 | 1134** |
| Fine aggregate (kg) | 576 | 576 | 611 |
| Water-cementitious material ratio | 0.23*** | 0.20*** | 0.23*** |
| Measured slump (mm) | 250 | 130 | 210 |

*Quantities adjusted for moisture content of aggregates
**Mix DM19-1 had a blend of 715 kg of 19 mm coarse aggregate and 419 kg of 9 mm coarse aggregate
***Not counting the water in the superplasticizer All cylinders were cured together at a constant temperature of 24 degrees C. under moist burlap enclosed by a polyethylene sheet. Compressive strength tests were conducted at 7, 14, 28, and 61 days using a loading rate of approximately 0.24 MPa/sec. Two different cylinder end conditions were, considered, namely, "regular" ground ends and capped ends with confining rings (confined caps according to the invention). Capping compound with the manufacturer's specified ultimate compressive strength of 35 MPa after 5 minutes and 55 MPa after 48 hours was used for the confined caps. Laboratory tests on this capping compound using 50×50×50 mm cubes produced ultimate compressive strengths of 44.2, 50.3, 49.5, and 51.1 MPa after 1, 24, 48, and 72 hours, respectively. All specimens were removed from the moist curing environment 24 hours prior to testing so that capping and grinding operations could be completed before testing. Cylinders were capped approximately one hour prior to being tested. All specimens were tested using a 2500 kN universal testing machine with the upper bearing block sphere 189 mm in diameter and the upper bearing block face 254 mm in diameter.

SPECIMEN END CONDITIONS

The confining rings were cut from steel pipe of standard wall thickness of 6.4 mm. Pipes with outside diameter of 125.6 mm and 175.6 mm were used as confining rings for the 100 mm and 150 mm diameter concrete cylinders, respectively. All confining rings were 10 mm in depth. The caps had a thickness of approximately 3 mm over the cylinder ends, and filled the 6.4 mm annulus between the confining ring and the specimen.

For end capping of a cylinder, one of the confining rings was placed in the recess in the base plate of the capping guide. This provides quick and accurate positioning of the confining ring. Molten capping compound was poured into the ring and the cylinder was guided into position by contact with the guide edges 34 to make the confined cap. For easy removal of the capped cylinder from the capping guide, a thin layer of oil was applied to the recess on the base plate before the confining ring was positioned into the recess and the melted sulfur compound was poured into the ring. The inner surface of the confining ring itself was kept oil-free. After a cap had been poured, the confining ring was left on the capped end until after the cylinder testing had been completed. Once both ends had been prepared in this manner, the cylinder was tested for its compressive strength in a usual manner.

Capping operations explained in the foregoing paragraphs are as simple as those used for normal strength concrete cylinders. The confining rings can be reused numerous times after the completion of a test.

COMPARISON OF TEST RESULTS

Figure 4:
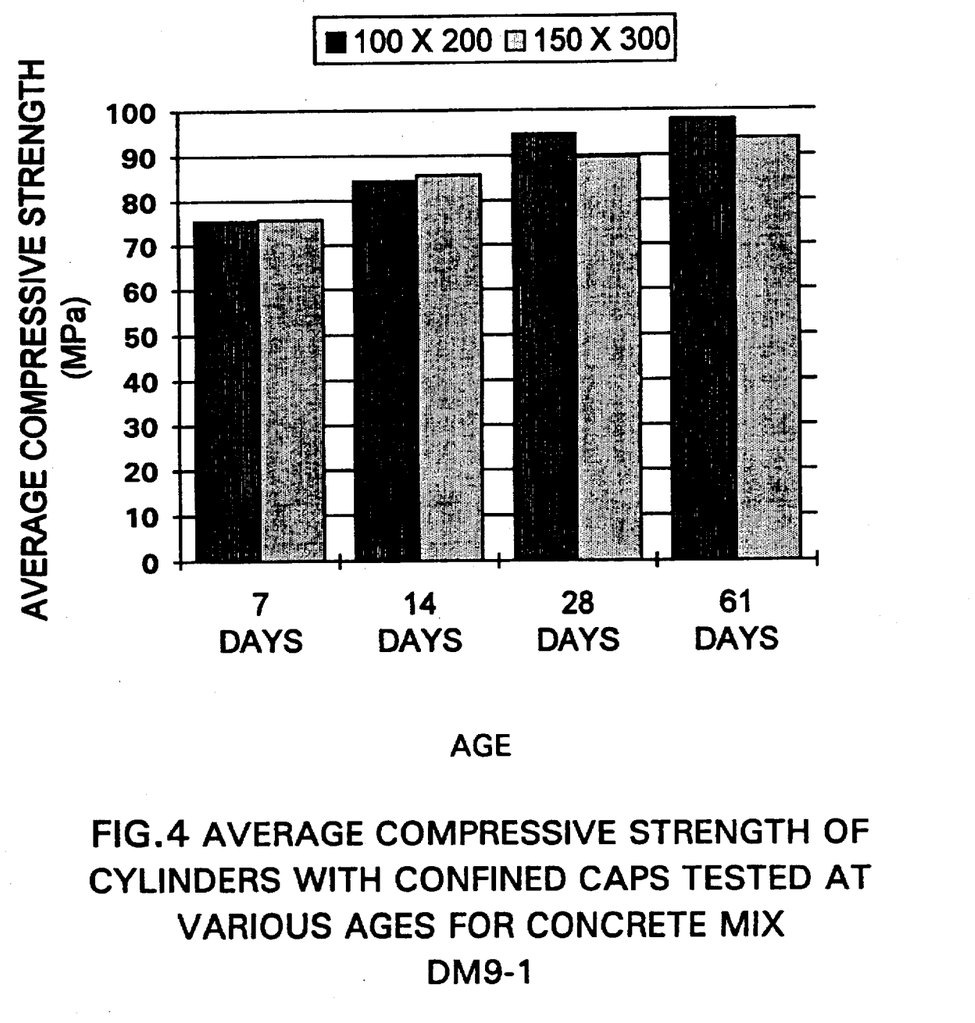
FIGS. 4 and 5 are graphs showing the average compressive strength of cylinders according to the invention, tested at various ages.
Figure 5:
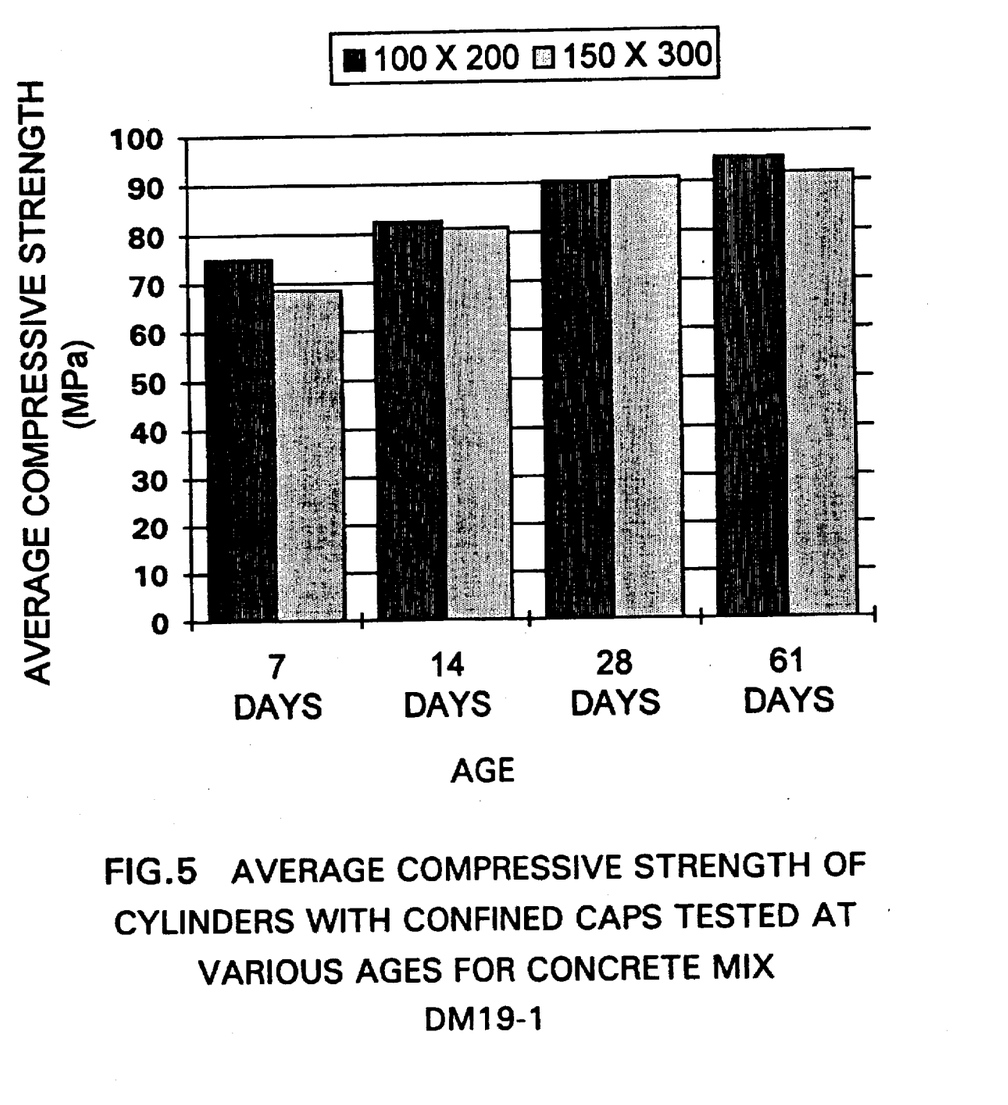

For maximum aggregate sizes of up to 19 mm, 100×200 mm cylinder test results are very consistent with those for 150×300 mm cylinders throughout the age range of 7 to 61 days, as shown in Table 2. The average compressive strengths given in this table are also plotted in FIGS. 4 and 5 for the DM9-1 and DM19-1 concrete mixes, respectively. The average relative strength of 100×200 mm specimens compared to 150×300 mm specimens is about 103% for each of the mixes considering all the ages. The average relative strength is also 103% for the combined set of cases from both mixes and the 28 and 61 day strengths taken as a group. The confined caps were used to prepare the ends of the specimens reported in Table 2 and FIGS. 4 and 5.

TABLE 2

Statistics of compressive strength of cylinders with confined caps tested at various ages*

| Cylinder size (mm) | 7-day strength | | 14-day strength | | 28-day strength | | 61-day strength | |
|---|---|---|---|---|---|---|---|---|
| | Average value (MPa) | Coefficient of variation (%) | Average value (MPa) | Coefficient of variation (%) | Average value (MPa) | Coefficient of variation (%) | Average value (MPa) | Coefficient of variation (%) |
| Mix DM9-1 | | | | | | | | |
| 100 × 200 | 75.4 | 1.6 | 84.4 | 4.9 | 94.8 | 2.6 | 97.9 | 1.6 |
| 150 × 300 | 75.7 | 1.9 | 85.7 | 0.9 | 89.6 | 2.6 | 93.8 | 1.9 |
| Mix DM 19-1 | | | | | | | | |
| 100 × 200 | 75.0 | 1.0 | 82.5 | 2.9 | 90.3 | 1.2 | 94.9 | 1.9 |
| 150 × 300 | 68.6 | 1.6 | 81.1 | 2.1 | 90.9 | 2.8 | 91..8 | 3.6 |

*Each value represents three tests for most cases

The compressive strength test results for the three high performance concrete mixes, obtained on the basis of two different cylinder sizes with two different cylinder end conditions, are presented in Tables 3 and 4. The average values and coefficients of variation for both 28 and 61 day strengths are reported in these tables. End conditions include ground ends and capped ends with confining rings. The test results presented for a given condition in Tables 3 and 4 are the averages from three test specimens, with a few exceptions.

TABLE 3

Average Compressive Strength (MPa) for Different End Conditions

| Cylinder size (mm) | 28-day strength | | 61-day strength | |
|---|---|---|---|---|
| | Ground ends | Ends with confined caps | Ground ends | Ends with confined caps |
| Mix DM9-1 | | | | |
| 100 × 200 | 98.2 | 94.8 | 102.6 | 97.9 |
| 150 × 300 | 91.6 | 89.16 | 95.6 | 93.8 |
| Mix DM9-2** | | | | |
| 100 × 200 | 107.7 | 105.5 | — | — |
| 150 × 300 | 106.8 | 102.6 | — | — |
| Mix DM19-1 | | | | |
| 100 × 200 | 96.3 | 90.3 | 94.9 | 94.9 |
| 150 × 300 | 89.5 | 90.9 | 94.7 | 91.8 |

*Each value represents the average of three tests for most cases
**Cylinders made from DM9-2 mix were tested only at 28 days An examination of the compressive strength coefficients of variation (Table 4) reveals that the 150×300 mm cylinders made from the DM19-1 mix produced a higher than expected coefficient of variation (5.9%) for one of the cases. The 100×200 mm cylinders made from the DM19-1 mix and both cylinder sizes in DM9-1 and DM9-2 mixes gave lower coefficients of variation (less than 5%), as indicated by Table 4. Hence, according to criteria for within-test coefficients of variation of laboratory batches established in ACI Committee 214, 1977; Recommended Practice for Evaluation of Strength Test Results of Concrete (ACL-214-77); ACI Manual of Concrete Practice, Part 1 (1989): 214-1 to 214-4, the concrete is classified as fair to excellent.

TABLE 4

Compressive Strength Coefficient of Variation (%) for Different End Conditions

| Cylinder size (mm) | 28-day strength | | 61-day strength | |
|---|---|---|---|---|
| | Ground ends | Ends with confined caps | Ground ends | Ends with confined caps |
| Mix DM9-1 | | | | |
| 100 × 200 | 1.5 | 2.6 | 1.8 | 1.6 |
| 150 × 300 | 4.5 | 2.6 | 1.9 | 1.9 |
| Mix DM9-2** | | | | |
| 100 × 200 | 2.1 | 2.6 | — | — |
| 150 × 300 | 0.9 | 3.6 | — | — |
| Mix DM19-1 | | | | |
| 100 × 200 | 1.9 | 1.2 | 5.0 | 1.9 |
| 150 × 300 | 5.9 | 2.8 | 2.6 | 3.6 |

Figure 6:
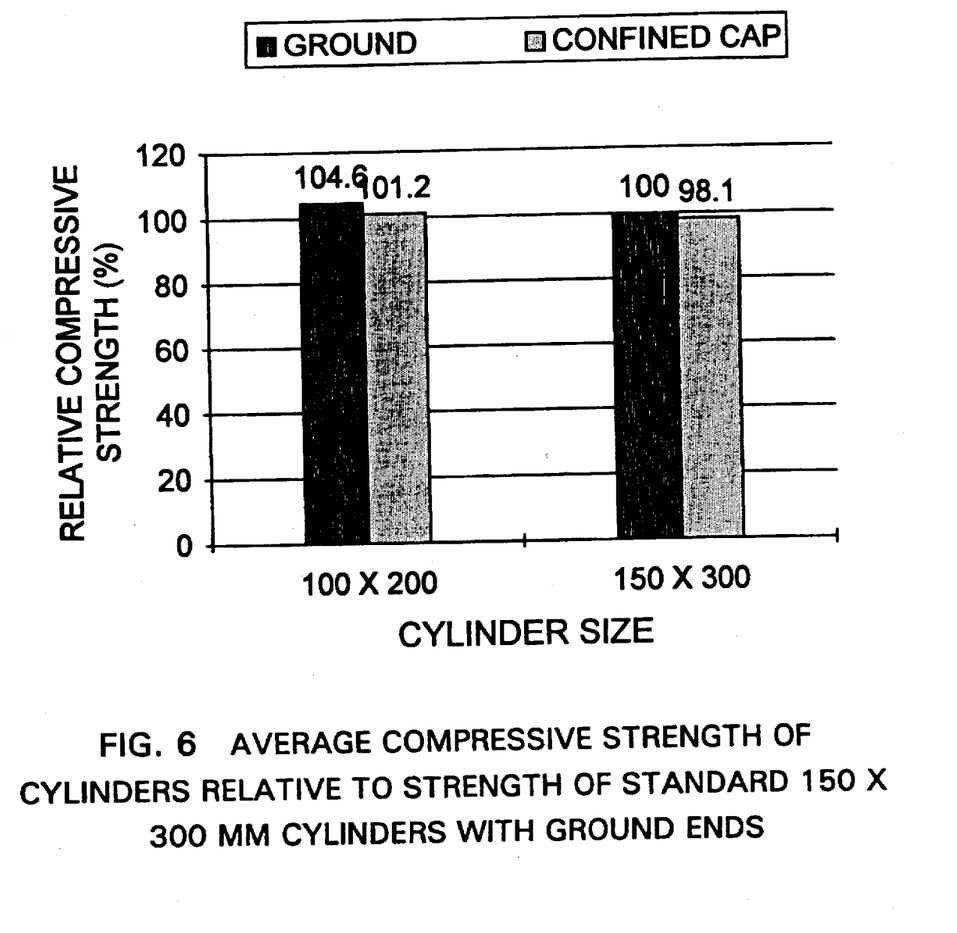
FIGS. 6 and 7 are graphs showing the average compressive strength of cylinders according to the invention relative to standard cylinders with ground ends.

*Each value represents the coefficient of variation of three tests for most cases
**Cylinders made from DM9-2 mix were tested only at 28 days For the purpose of making comparisons, the compressive strength of a 150×300 mm cylinder with ground ends is taken to represent the "standard" compressive strength. Relative compressive strengths for both the other cylinder size (100×200 mm) and the confined cap end condition are compared to the "standard" in FIG. 6. Each relative strength value in FIG. 6 is the average of approximately 15 tests. This includes the test data from all three concrete mixes and both test ages given in Table 3.

As shown in FIG. 6, the average relative test strengths for cylinders utilizing confined caps are very close to those for the "standard" 150×300 mm test specimens with ground ends. For the 150×300 mm cylinders with confined caps, the relative strength is 98.1% of the "standard" strength. The results for the 100×200 mm cylinders are also in close agreement with those of the "standard" strength considering the effect of cylinder size, with relative strengths of 101.2% and 104.6% for confined caps and ground ends, respectively. However, the dispersion in the test data is somewhat larger for cylinders with ground ends. The coefficients of variation for individual groups of data in Table 4 vary from 0.9% to 5.9% for cylinders with ground ends and from 1.2% to 3.6% for cylinders with confined caps. This indicates that it may be slightly more difficult to get consistency in test results from specimens with ground end conditions. Imperfections resulting in a non-plane ground surface can affect the failure mode of a specimen and thus the measured cylinder strength. In this context, it may be noted that, for the results reported here, the cylinders were ground at the Ontario Ministry of Transportation Laboratory in Thunder Bay, Ontario, Canada and are expected to represent the typical ground end conditions for the industry.

Figure 7:
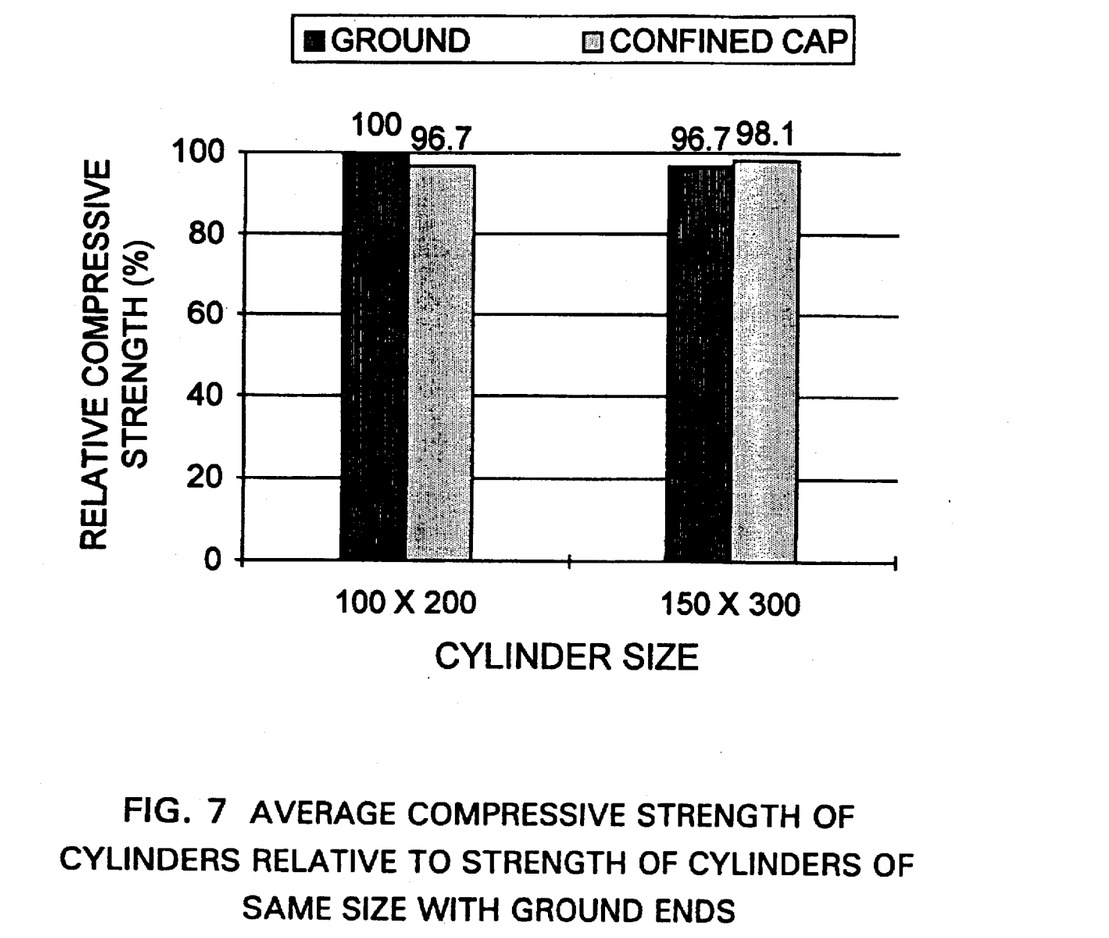

The relative compressive strengths of cylinders with confined capped ends are compared, in FIG. 7, to the strength of cylinders of the same respective sizes but with ground end conditions. Each relative strength in FIG. 7 represents the average of approximately 15 tests. This includes the test data from all three concrete mixes and both test ages given in Table 3. The results are very similar to those discussed previously. Cylinders tested using the confined caps have relative compressive strengths in close agreement with specimens of the same size having ground ends. For cylinders 150×300 mm and 100×200 mm in size, the relative strengths with confined caps are 98.1% and 96.7%, respectively, as indicated by FIG. 7.

After failure the cylinders with confined caps have conical type failure modes very similar to those obtained for cylinders with ground ends.

The confined capping system of the present invention provides a simple, inexpensive approach for the compressive strength testing of high performance concrete cylinders. This approach ensures that confinement is provided to the cap without having to place tight controls on the cylinder end roughness prior to capping and on the cap thickness. The method has been successfully used for concrete strengths in excess of 100 MPa. Compressive strength test results obtained from both 150×300 mm and 100×200 mm cylinders tested using confined caps are both in good agreement with the "standard" measured compressive strength of 150×300 mm cylinders with ground end conditions.

While certain embodiments of the invention have been described in the foregoing, it is to be understood that the invention is not limited to those embodiments. The specimens described in the foregoing are cylindrical, but other specimen configurations, for example prisms, may be equipped with confined caps in the same way. The ring dimensions will vary with the properties of the material from which they are made. In the capping guide, the cylinder may be centered using an angle iron or any other appropriate structure. Other modifications will occur to those knowledgable in the art. The invention is therefore to be considered limited solely by the scope of the appended claims.

We claim:

1. A method of preparing for compressive strength testing an end of a high performance concrete specimen having an anticipated minimum compressive strength of at least 70 MPa, the method comprising:

providing a test specimen of the high performance concrete;

providing a confining ring;

capping one end of the test specimen with a capping compound in direct engagement with the end of the specimen, the capping compound having a compressive strength substantially less than said anticipated minimum compressive strength, comprising:
  (i) melting the capping compound;
  (ii) filling the ring with liquid capping compound;
  (iii) placing the end of the test specimen into the capping compound within the ring; and
  (iv) allowing the capping compound to solidify.

2. A method according to claim 1 comprising repeating the capping steps for the other end of the specimen.

3. A method according to claim 1 wherein the specimen is cylindrical.

4. A test specimen of high performance concrete having a minimum compressive strength of at least 70 MPa, said specimen comprising:

an elongate member of the concrete, the member having opposite ends;

two caps covering respective ones of the opposite ends of the member, each cap comprising a sulphur capping material covering the end of the member, in direct contact therewith and a ring surrounding the cap circumferentially, the ring having a tensile strength greater than that of the capping material.

5. A test specimen according to claim 4 wherein the ring has an inside diameter greater than an outside diameter of the specimen.

6. A test specimen according to claim 5 wherein the capping material of the disk has a thickness of less than a height of the ring.

7. A test specimen according to claim 6 wherein the capping material overlaps a cylindrical side of the concrete specimen to fill an annular space between the ring and the specimen.

8. A test specimen according to claim 4 wherein the disk thickness is approximately 3 mm.

9. A test specimen according to claim 4 wherein the ring is a steel ring.

10. A test specimen according to claim 9 wherein the ring thickness is approximately 6.4 mm.

11. A test specimen according to claim 10 wherein the ring height is approximately 10 mm.

12. Apparatus for preparing a test specimen of high performance concrete, said apparatus comprising:

a base plate having a smooth upper surface;

ring confining means on the base plate for holding a confining ring at a predetermined position on the base plate; and specimen centering means for engaging a specimen of the concrete and centering the specimen on the ring.

13. Apparatus according to claim 12 wherein the ring centering means comprise a circular recess in the base plate.

14. Apparatus according to claim 12 wherein the specimen centering means comprise two abutment means for engaging the side of the specimen above the ring centering means.

15. Apparatus according to claim 14 wherein the specimen centering means comprise a channel and means for mounting the channel on the base with two flanges of the channel having parallel edges substantially perpendicular to the base plate.

* * * * *